(12) United States Patent
Jarvis et al.

(10) Patent No.: US 10,876,125 B2
(45) Date of Patent: Dec. 29, 2020

(54) DNA RECOMBINATION

(71) Applicants: UNIVERSITY OF PLYMOUTH, Devon (GB); THE REGENTS OF THE UNIVERSITY OF CALIFORNIA, Oakland, CA (US)

(72) Inventors: Michael Jarvis, Devon (GB); Aisling Murphy, Devon (GB); Peter Barry, Davis, CA (US)

(73) Assignees: UNIVERSITY OF PLYMOUTH, Devon (GB); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 7 days.

(21) Appl. No.: 15/751,426

(22) PCT Filed: Aug. 5, 2016

(86) PCT No.: PCT/EP2016/068782
§ 371 (c)(1),
(2) Date: Feb. 8, 2018

(87) PCT Pub. No.: WO2017/025472
PCT Pub. Date: Feb. 16, 2017

(65) Prior Publication Data
US 2018/0237788 A1    Aug. 23, 2018

(30) Foreign Application Priority Data
Aug. 8, 2015 (GB) .................. 1514034.6

(51) Int. Cl.
C12N 15/79 (2006.01)
C12N 15/10 (2006.01)
C12N 15/86 (2006.01)
C12N 15/74 (2006.01)

(52) U.S. Cl.
CPC .......... *C12N 15/79* (2013.01); *C12N 15/102* (2013.01); *C12N 15/74* (2013.01); *C12N 15/86* (2013.01); *C12N 2310/20* (2017.05); *C12N 2710/16143* (2013.01); *C12N 2760/14134* (2013.01)

(58) Field of Classification Search
None
See application file for complete search history.

(56) References Cited

U.S. PATENT DOCUMENTS

| | | | |
|---|---|---|---|
| 2004/0219516 A1* | 11/2004 | Bennett ............... | C12N 15/86 435/5 |
| 2010/0291653 A1* | 11/2010 | Ness ................... | C12N 15/815 435/171 |
| 2012/0258487 A1* | 10/2012 | Chang ................. | C12N 15/10 435/34 |

FOREIGN PATENT DOCUMENTS

| | | |
|---|---|---|
| CN | 101619324 | 1/2010 |
| WO | 03012036 | 2/2003 |
| WO | 2009132863 | 11/2009 |
| WO | 2011019717 | 2/2011 |
| WO | 2011143653 | 11/2011 |

OTHER PUBLICATIONS

Eberhardt et al., Strategy for deletion of complete open reading frames in *Saccharomyces cerevisiae*, Current Genetics, vol. 27, pp. 306-308, 1995 (Year: 1995).*
Jung et al., Cloning of polymerase chain reaction-generated DNA containing terminal restriction endonuclease recognition sites; Methods in Enzymology, vol. 218, pp. 357-362, 1990 (Year: 1990).*
Chou et al. (2015) A series of conditional shuttle vectors for targeted genomic integration in budding yeast. FEMS Yeast Research, 15(3):pp. 1-9 (Year: 2015).*
Weinberg, Suzanna—European Patent Office as ISA "International Search Report and Written Opinion—PCT/EP2016/068782" pp. 1-20.
Marzi, Andrea et al. "Cytomegalovirus-based vaccine expressing Ebola virus glycoprotein protects nonhuman primates from Ebola virus infection" Scientific Reports; Feb. 15, 2016; pp. 1-10.
Chu, Van Trung et al. "Increasing the efficiency of homology-directed repair for CRISPR-Cas9-induced precise gene editing in mammalian cells" Nature Biotechnology; vol. 33:5; May 2015; pp. 1-10
Lu, Zhuo-Zhuang et al. "Novel recombinant adenovirus type 41 vector and its biological properties" The Journal of Gene Medicine 2009; 11: pp. 128-138.

(Continued)

*Primary Examiner* — Neil P Hammell
(74) *Attorney, Agent, or Firm* — Nicholas J. Landau; Jessica Zurlo; Bradley Arant Boult Cummings LLP (57) ABSTRACT

There is provided a non-PCR based method for construction of a DNA recombination fragment with necessary flanking regions homologous to a desired site of genetic manipulation within a target DNA required for recombination-based manipulation of said target DNA, comprising the steps of: A) identifying a desired site of insertion for a genetic element in said target DNA; B) locating an endogenous, native, half-site of a selected restriction endonuclease present upstream of the site within the DNA to be targeted for genetic manipulation and thereby defining the 5' extent of an upstream homology region; C) locating an endogenous, native, half-site of the same selected restriction endonuclease present downstream of the site within the DNA to be targeted for genetic manipulation and thereby defining the 3' extent of a downstream homology region; D) synthesising a flanking region cassette resulting in juxtapositioning of the upstream and downstream half-sites thereby causing formation of complete restriction site for the selected restriction endonuclease flanked by said upstream and downstream homology regions; and E) inserting the flanking region cassette into a plasmid vector which includes the genetic element to be used to manipulate the target DNA, conferring upon the plasmid vector the necessary flanking homology regions for recombination within the said target DNA at the desired site of insertion.

12 Claims, 8 Drawing Sheets

(56) References Cited

OTHER PUBLICATIONS

Angrand, Pierre-Olivier et al. "Simplified generation of targeting constructs using ET recombination" Nucleic Acids Research, 1999, vol. 27:17; pp. 1-6.
Gaj, Thomas et al. "ZFN, TALEN, and CRISPR/Cas-based methods for genome engineering" Trends in Biotechnology (2013) pp. 1-9
Monteiro, Freddy et al. "A Chromosomal Insertion Toolbox for Promoter Probing, Mutant Complementation, and Pathogenicity Studies in Ralstonia solanacearum" MPMI vol. 25, No. 4, 2012, pp. 557-568.
Hastings, P.J. et al. "Ends-In vs. Ends-out Recombination in Yeast" Genetics 135: 973-980 (Dec. 1993).
"Search Report—GB patent application No. GB1508136.7" Feb. 26, 2016; pp. 1-6.

\* cited by examiner

FIG. 3B 140 kDa —

(anti-EBOV GP)

Lanes (3A): [WT], [1-4], [1-5], [1-12], [2-1]

Lanes (3B): [2-1A], [2-1B], [3-12A], [3-12B], [3-12C], [3-14A]

FIG. 5B 140 kDa — (Anti-EBOV GP)

__DNA RECOMBINATION__

CROSS-REFERENCE TO RELATED APPLICATIONS

This application is a national stage under 35 U.S.C. 371 of International Application No. PCT/EP2016/068782 having an international filing date of Aug. 5, 2016 (currently published). International Application No. PCT/EP2016/068782 cites the priority of GB 1514034.6, filed Aug. 8, 2015 (abandoned).

BRIEF DESCRIPTION OF THE DRAWINGS

FIG. 2: Exemplary embodiment of the method to clone GP of EBOV under control of the endogenous RhCMV Rh25 promoter, thereby producing a recombinant RhCMV expressing EBOV GP under the RhCMV Rh25 promoter. A) Schematic for insertion of EBOV GP within rhesus cytomegalovirus (RhCMV) genome to place under control of endogenous Rh25 (UL9) (late) promoter. 'A' (5'-AAAC-3') and 'C' (5'-AAAC-3' on reverse strand) represent endogenous 'half sites' of PmeI (GTTTAAAC) in ¬flanking homology region (HR) upstream and downstream of target site for insertion. B) FRC with the 'new' single PmeI site and necessary restriction sites (NheI and MfeI) for insertion into the pminiOri (suicide-based vector). C) The FRC was cloned into the pminiOri (suicide-based vector) containing the EBOV GP for insertion into the RhCMV genome. D) Schematic of resulting plasmid. E) PmeI digestion was used to linearize the recombination fragment, which contains the necessary flanking HR for E/T based recombination within the RhCMV genome. 5' Phosphate residues are shown for DNA strand orientation.

FIG. 4: Embodiment of the method to clone GP of EBOV under control of the endogenous RhCMV Rh220 promoter, thereby producing a recombinant RhCMV expressing EBOV GP under the RhCMV Rh220 promoter. A) Schematic for insertion of EBOV GP within rhesus cytomegalovirus (RhCMV) genome to place under control of endogenous Rh220 (US28.5) (E) promoter. B) FRC with the 'new' single PmeI site and necessary restriction sites (NheI and MfeI) for insertion into the pminiOri (suicide-based vector). C) The FRC was cloned into the pminiOri (suicide-based vector) containing the EBOV GP for insertion into the RhCMV genome. D) Schematic of resulting plasmid. E) PmeI digestion was used to linearize the recombination fragment, which contains the necessary flanking HR for E/T or CrispR-based recombination within the RhCMV genome. 5' Phosphate residues are shown for DNA strand orientation.

FIG. 6: Embodiment of the method to clone GP of EBOV under control of the heterologous human EFI alpha promoter, thereby producing a recombinant RhCMV expressing EBOV GP under the human EFI alpha promoter. A) Schematic for insertion of EBOV GP within rhesus cytomegalovirus (RhCMV) genome to place under control of a heterologous promoter. 'A' (5'-AAAC-3') and 'C' (5'-AAAC-3' on reverse strand) represent endogenous 'half sites' of PmeI (GTTTAAAC) in flanking homology region (HR) upstream and downstream of target site for insertion. B) FRC with the 'new' single PmeI site and necessary restriction site (MfeI) for insertion into the pminiOri (suicide-based vector). C) The FRC was cloned into the pminiOri (suicide-based vector) containing the EBOV GP for insertion into the RhCMV genome. D) Schematic of resulting plasmid. E) PmeI digestion was used to linearize the recombination fragment, which contains the necessary flanking HR for E/T based recombination within the RhCMV genome. 5' Phosphate residues are shown for DNA strand orientation.

FIG. 8: Embodiment of the method with proposed use of CrispR/Cas9 technology using cloning of GP of EBOV under control of the heterologous human EFI alpha promoter. A) PmeI half sites will be selected located 634 bp upstream (nt 215,598) and 731 bp (nt 216,964) downstream of desired site of insertion (*) (between 216,232 and 216,233). B) FRC with the 'new' single PmeI site, as well as MfeI sites for insertion into EcoRI of pminiOri EFI alpha/EBOV GP (a suicide-based vector). C) The FRC will be cloned into the EFI alpha EBOV/GP miniOri for insertion into the RhCMV genome. D) Schematic of resulting plasmid. Note: EFI alpha EBOVGP ORF runs in X to Y direction on 'Genetic Element for Insertion'. E) PmeI digestion will be used to linearize the recombination fragment, which now contains the necessary flanking homology regions (HR) for CrispR/Cas9-based recombination within the RhCMV genome. F) The rt-flanked KanR+TK/GFP cassette is removed from recombinant RhCMV virus genome by co-expression of FLP recombinase (using a FLP expression plasmid) in the presence of negative selection for TK (gancyclovir). 5' Phosphate residues are shown for DNA strand orientation. (*) Site for genetic element insertion within RhCMV genome (numbering based on Malouli et al. 2012; Acc # JQ795930) within rh213 and Rh214 intergenic region. 'A' (5'-AAAC-3') and 'C' (5'-AAAC-3' on reverse strand) represent endogenous 'half sites' of PmeI: GTTTAAAC (a rare 8nt cutter).

DETAILED DESCRIPTION

The present invention relates generally to DNA recombination and particularly to a method for production of DNA recombination fragments with necessary flanking regions homologous to a desired site of genetic manipulation within a target DNA required for recombination-based manipulation of the target DNA. As such, the present invention relates to CrispR/Cas9-based, E/T-based and other recombination-based technologies that use such DNA fragments as an integral part of their recombination systems.

Recombination mechanisms are still incompletely defined, but involve the copying, cutting and covalent joining of DNA sequences. Recombination can occur between two different DNA molecules (intermolecular recombination) or between two regions of a single DNA molecule (intramolecular recombination).

The present invention provides a method of inserting desired genetic element(s) into any target genome comprised of recombination of a homology-flanked genetic element(s), formed as described herein, into the said target genome.

The present invention also relates to techniques for rapid genetic manipulation of viruses and virus-based vectors. The target DNA may be a viral genome; for example a herpesvirus genome such as CMV.

According to an aspect of the present invention there is provided a non-PCR based method for construction of a DNA recombination fragment with necessary flanking regions homologous to a desired site of genetic manipulation within a target DNA required for recombination-based manipulation of said target DNA.

An overview of this invention being used for manipulation of a DNA virus (herpesvirus) genome is shown graphically. Subsequent figures contain examples of where this invention has been reduced to practice.

Figure 1:
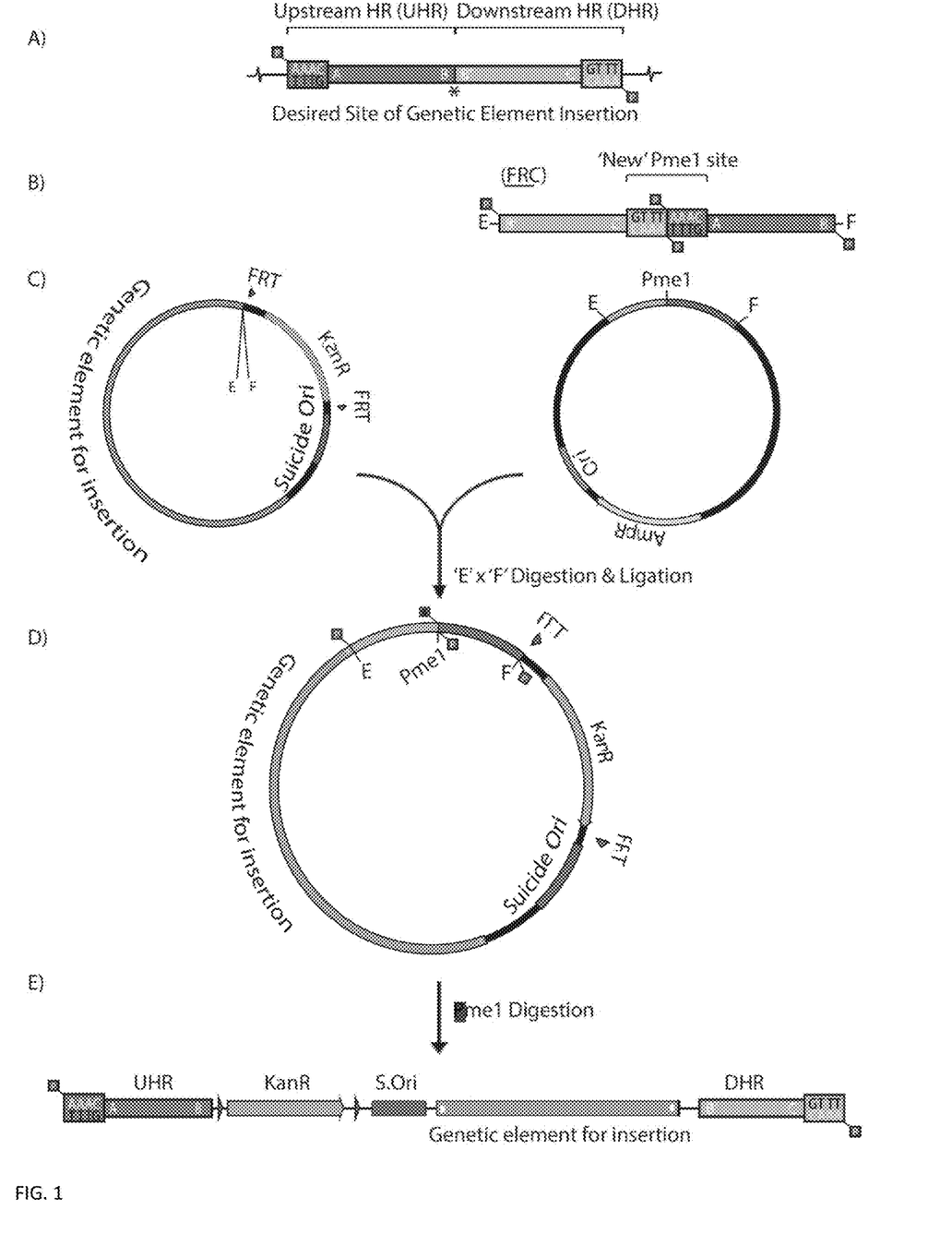
FIG. 1: An overview of an embodiment of the system. A) Representation of site for genetic element insertion within herpesvirus genome. B) A flanking region cassette (FRC) with a single site and necessary restriction sites (E and F) for insertion into the pminiOri (suicide-based vector) are then synthesized. C) The FRC is cloned into the respective miniOri (suicide-based vector) containing the genetic element for insertion into the herpesvirus genome. D) Schematic of resulting plasmid. E) PmeI digestion is used to linearize the recombination fragment, which contains the necessary flanking homology regions (HR) for E/T based recombination within the herpesvirus genome. 5' Phosphate residues are shown for DNA strand orientation.

An aspect of the invention is comprised of the following steps:
A) identifying a desired site of insertion for a genetic element in said target DNA (Overview Figure, A);
B) locating an endogenous (native) half-site of a selected restriction endonuclease present upstream of the site within the DNA to be targeted for genetic manipulation and thereby defining the 5' extent of the upstream homology region (Overview Figure, A);
C) locating an endogenous (native) half-site of the same selected restriction endonuclease present downstream of the site within the DNA to be targeted for genetic manipulation and thereby defining the 3' extent of the downstream homology region (Overview Figure, A);
D) synthesising a flanking region cassette (FRC) resulting in juxtapositioning of the upstream and downstream half-sites thereby causing formation of complete restriction site for the selected restriction endonuclease flanked by said upstream and downstream homology regions (Overview Figure, B); and
E) inserting the FRC into a plasmid vector which includes the genetic element(s) to be used to manipulate the target DNA, conferring upon the plasmid vector the necessary flanking homology regions for recombination within the said target DNA at the desired site of insertion (Overview Figure, C & D).

A second aspect of this invention utilises heterologous (non-native) half-sites, which are not present within the native DNA sequence of the flanking target genome. This use of heterologous (non-native) half-sites is the only difference between the two versions of this invention. Non-native half-sites can be used if the recombination technology being exploited for genetic manipulation of the target DNA does not require native sequence at the ends of the DNA recombination fragment.

This modification of the invention is comprised of the following steps:
A) identifying a desired site of insertion for a genetic element in said target DNA;
B) selection of heterologous (non-native) half-sites of a selected restriction endonuclease, with restriction site selection being based on absence of the restriction site in its complete form within upstream and downstream homology regions flanking the DNA region to be targeted;
C) synthesising a FRC including upstream and downstream homology regions and resulting in juxtapositioning of the upstream and downstream flanking homology regions separated by their non-native half-sites thereby causing formation of a complete restriction site for the selected restriction endonuclease flanked by the homology regions; and
D) inserting the FRC into a plasmid vector which includes the genetic element(s) to be used to manipulate the target DNA; conferring upon the vector the necessary flanking homology regions for recombination within the genome at the target site.

The method further comprises the step of linearising the vector by using the selected restriction endonuclease to cut within the FRC to form a recombination fragment, whereby the recombination fragment has the necessary flanking homology regions to direct recombination within the genome at the target site.

The restriction endonuclease site may be selected on the basis that it is not present within either the flanking homology region or genetic element used during manipulation of the target DNA.

In some embodiments the upstream and downstream homology regions are at least 50 nucleotides in length (e.g. the size required for efficient E/T-based recombination). In other embodiments the regions are at least 500 nucleotides in length (e.g. the size required for efficient CrispR/Cas9 recombination). Other recombination technologies may require additional homology region sizes.

The recombination fragment made using this invention may, for example, be inserted using E/T-based recombination or CrispR/Cas9-based recombination, or other recombination technologies (eg., RecA-based).

The present invention in one aspect or embodiment may provide a method of generating a recombination fragment for genetic manipulation of a viral genome using E/T-based or CrispR/Cas9-based recombination, or other recombination technologies (eg., RecA-based) that uses a plasmid vector or recombination fragment formed according to a method as described herein into a viral genome.

This invention in other aspects or embodiments may be used for rapid construction of herpesvirus-based vaccines against emerging infectious disease (EID) pathogens. Most biologically significant (i.e., deadly and transmissible) 'high-risk' pathogens: I) Erupt from EID 'hotspot' regions of the world (frequently politically unstable developing countries at lower latitudes); 2) Transmit to humans 'zoonotically' (i.e., from animals to humans) either directly, or indirectly through domestic animals (horses, pigs, etc.), from a small number of 'high-value' wildlife species (rodents, bats and non-human primates); and 3) Exist as RNA viruses never previously encountered. To date there is no robust means to control emergence of these high-risk pathogens either in wildlife species or in domestic animals. It is known that most viral high-risk pathogens tested can be immunologically targeted through vaccination, commonly by using their major surface protein as the target antigen.

Experience with rabies in temperate regions also shows that effective vaccination of wildlife has the capacity to prevent zoonotic transmission. However, vaccination of wildlife (or domestic animals involved in transmission) under more extreme conditions present in EID 'hotspots' is currently an insurmountable problem for conventional vaccination that requires individual inoculation of each animal for induction of immunity.

The present invention provides a method of rapidly constructing a recombinant virus or virus-based vaccine comprising the step of CrispR/Cas9-based recombination of a plasmid vector or recombination fragment formed according to a method as described herein into a viral genome. When combined with effective pre-emptive surveillance, such an embodiment will provide a means to pre-emptively remove an imminent EID threat at its source prior to establishment in humans.

In one aspect and embodiment, the present invention, in combination with rapid recombination technologies such as CrispR/Cas9, is used to construct a 'single-shot' herpesvirus-based vaccine able to provide durable, long-lasting levels of protective immunity against after a single dose.

In another aspect or embodiment, the present invention, in combination with a rapid recombination technology such as CrispR/Cas9, is used to construct a 'self-disseminating' (SD) vaccine. SD vaccines exploit the ability of replicating herpesvirus-based vectors to spread through their animal host populations without the need for direct inoculation of every animal. In this embodiment, the invention is used to rapidly produce a SD vaccine against an identified EID pathogen threat, which can be utilized to inoculate a limited number of 'founder' animals of the involved animal species. As the SD vaccine is engineered to express target antigens from the EID pathogen of interest, spread from vaccinated to non-vaccinated animals of the SD vaccine results in coordinate spread of EID specific immunity throughout the targeted animal population.

In one aspect or embodiment, the invention is used in combination with CRISPR/Cas9, or similarly rapid recombination technology for rapid construction of single-shot or SD vaccines as a means to enable effective immunological targeting of high-risk pathogens in wildlife (or domestic animals involved in transmission) in EID hotspots.

In combination with CrispR/Cas9 technology, the invention uses replicating herpesviruses for vaccine construction. This is in contrast to BAC-based approaches, which use a single herpesvirus genome maintained as a BAC. In addition to increasing the speed of vaccine construction, this use of genetically non-identical mixtures of viruses as the genetic background for the CrispR/Cas9-based cloning diminishes potential problems associated with BAC-based cloning, which necessarily use a single parental genotype that may in some cases be unknowingly attenuated.

The vaccine may comprise a herpesvirus-based vector, for example a CMV-based vector.

The CMV-based vector may be selected from, but is not limited to, human CMV (HCMV), simian CMV (SCCMV), rhesus macaque CMV (RhCMV), chimpanzee CMV (CCMV) murine CMV (MCMV), gorilla CMV (GoCMV) and porcine CMV (PCMV).

The herpesvirus-based vector may additionally be selected from, but is not limited to, bovine herpesvirus 4 (BoHV-4), equine herpesvirus 2 (EHV-2), mustelid herpesvirus I (MusHV-I).

The present invention also provides technology to construct a vaccine consisting of, comprising or including a vector as described herein.

The present invention also provides a composition comprising the vaccine or vector as described herein and a pharmaceutically acceptable carrier.

The present invention also provides a method for production of a vaccine to treat a subject with an infectious disease, or at risk of becoming infected with an infectious disease comprising selecting a subject in need of treatment and administering to the subject the recombinant vector, vaccine or composition as described herein.

The subject may be, for example, a human or an animal (such as wildlife or a domestic animal).

The present invention also provides a method for production of a vaccine, vector or composition as described herein for the prevention or treatment of a disease.

The present invention may be applicable to veterinary and human infectious disease control and human and animal medicine.

In some aspects and embodiments the present invention relates to an improvement to recombination systems, which results from the new PCR-independent production method of the necessary DNA recombination fragments (genetic elements) for insertion within a target genome.

In a further aspect the present invention provides a method for PCR-independent production of a DNA recombination fragment with necessary flanking regions homologous to a desired site of genetic manipulation within a target DNA required for recombination-based manipulation of said target DNA, comprising the steps of:

A) locating respective endogenous (native) 'half-sites' of a selected restriction endonuclease present upstream and downstream of the site within the DNA to be targeted for genetic manipulation. Alternatively, non-endogenous (non-native) half-sites that are not present within the DNA region to be targeted may be used.
B) synthesising (using any existing DNA synthesis technology) a FRC resulting in juxtaposition of selected 'half-sites' thereby causing formation of complete restriction site for the selected restriction endonuclease.
C) inserting the FRC into a circular vector which includes the genetic element to be used to manipulate the target DNA.
D) linearising the vector (if linearization is required for said recombination being used) by using the selected restriction endonuclease to cut within the cassette to form a recombination fragment, whereby the recombination fragment has the necessary flanking homology regions for recombination within the genome at the target site.

The upstream and downstream flanking arms may be positioned as shown in accompanying figures.

Following insertion into a circular DNA vector that contains any additional genetic information to be inserted into the target DNA molecule during its manipulation, cleavage with the restriction enzyme results in a recombination fragment with required upstream and downstream homologous regions (if linearization is required for said recombination system being used).

The endonuclease may be a rare cutter and not present within either the flanking homology region or genetic element used during manipulation of the target DNA, as would be apparent to a person generally skilled in the art of molecular biology. A rare-cutter enzyme is a restriction enzyme with a recognition sequence that occurs only rarely in a genome. For example, rare-cutter enzymes with 8-nucleotide recognition sites cut on average once every $4^8$ bp (65,536 bp).

The use of endogenous (native) 'half-sites' in the present invention enables insertion of desired DNA modification into target genome without addition of any additional, heterologous information to the target genome at the extreme ends of the flanking homology regions.

The present invention also provides a method of combating an EID pathogen following identification of an emerging disease threat comprising the steps of rapidly synthesizing a recombinant virus or virus-based vaccine using one or more method steps as described herein.

The present invention may provide a method for creating a CMV vector, for example for the treatment of cancer, or the treatment of an infectious pathogen-based disease.

Different aspects and embodiments of the invention may be used separately or together.

Further particular and preferred aspects of the present invention are set out in the accompanying independent and dependent claims. Features of the dependent claims may be combined with the features of the independent claims as appropriate, and in combination other than those explicitly set out in the claims.

The present invention will now be more particularly described, by way of example, with reference to the accompanying drawings.

The example embodiments are described in sufficient detail to enable those of ordinary skill in the art to embody and implement the systems and processes herein described. It is important to understand that embodiments can be provided in many alternate forms and should not be construed as limited to the examples set forth herein.

Accordingly, while embodiment can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

Unless otherwise defined, all terms (including technical and scientific terms) used herein are to be interpreted as is customary in the art. It will be further understood that terms in common usage should also be interpreted as is customary in the relevant art and not in an idealised or overly formal sense unless expressly so defined herein.

FIG. 1—Overview of EZ-Recombination System

Overview of EZ-Recombination System.

A) Representation of site for genetic element insertion within herpesvirus genome. (5'-AAAC-3') and 'C' (5'-AAAC-3' on reverse strand) represent endogenous 'half sites' of rare (8nt cutters) (in this case, PmeI: GTTTAAAC) that will be present on average once every 256nt within the upstream and downstream endogenous sequence of the target site for insertion. The particular 8nt restriction enzyme sequence selected is based on i) its absence from flanking regions, and ii) absence from within the suicide-based vector containing the heterologous genetic element for insertion.

B) A Flanking Region Cassette (FRC) with the 'new' single PmeI site and necessary restriction sites (E and F) for insertion into the pminiOri (suicide-based vector) are then synthesized (using an AmpR carrier vector—generally gene synthesis has been performed by GeneArt from Invitrogen).

C) The FRC is cloned into the respective miniOri (suicide-based vector) containing the genetic element for insertion into the herpesvirus genome.

D) Schematic of resulting plasmid.

E) PmeI digestion is used to linearize the recombination fragment, which contains the necessary flanking homology regions (HR) for E/T based recombination within the herpesvirus genome. 5' Phosphate residues are shown for DNA strand orientation.

Figure 2:
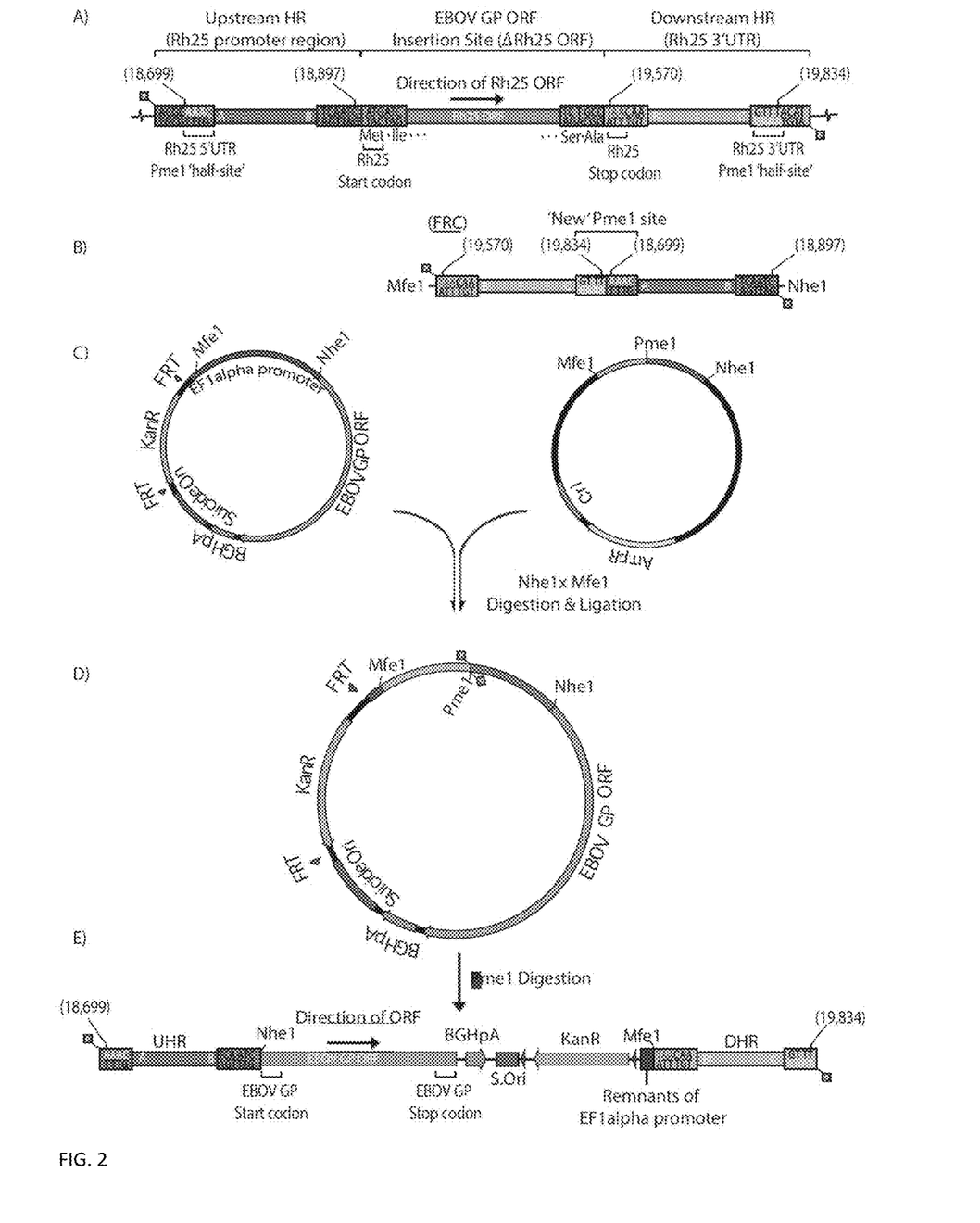

FIGS. 2 and 3—Reduction to Practice, Example 1. Using the Invention to Clone GP of EBOV Under Control of the Endogenous RhCMV Rh25 Promoter, Thereby Producing a Recombinant RhCMV Expressing EBOV GP Under the RhCMV Rh25 Promoter.

Reduction to Practice of EZ Recombination System II.

FIG. 2A) Schematic for insertion of EBOV GP within rhesus cytomegalovirus (RhCMV) genome to place under control of endogenous Rh25 (UL9) (late) promoter. 'A' (5'-AAAC-3') and 'C' (5'-AAAC-3' on reverse strand) represent endogenous 'half sites' of PmeI (GTTTAAAC) in flanking homology region (HR) upstream and downstream of target site for insertion. PmeI was selected based on i) its absence from flanking regions, and ii) absence from within the suicide-based vectors containing the EBOV GP for insertion.

FIG. 2B) FRC with the 'new' single PmeI site and necessary restriction sites (NheI and Mfe 1) for insertion into the pminiOri (suicide-based vector) was synthesized (using an AmpR carrier vector from GeneArt from Invitrogen).

FIG. 2C) The FRC was cloned into the pminiOri (suicide-based vector) containing the EBOV GP for insertion into the RhCMV genome.

FIG. 2D) Schematic of resulting plasmid.

FIG. 2E) PmeI digestion was used to linearize the recombination fragment, which contains the necessary flanking HR for E/T based recombination within the RhCMV genome. 5' Phosphate residues are shown for DNA strand orientation.

Figure 3A:
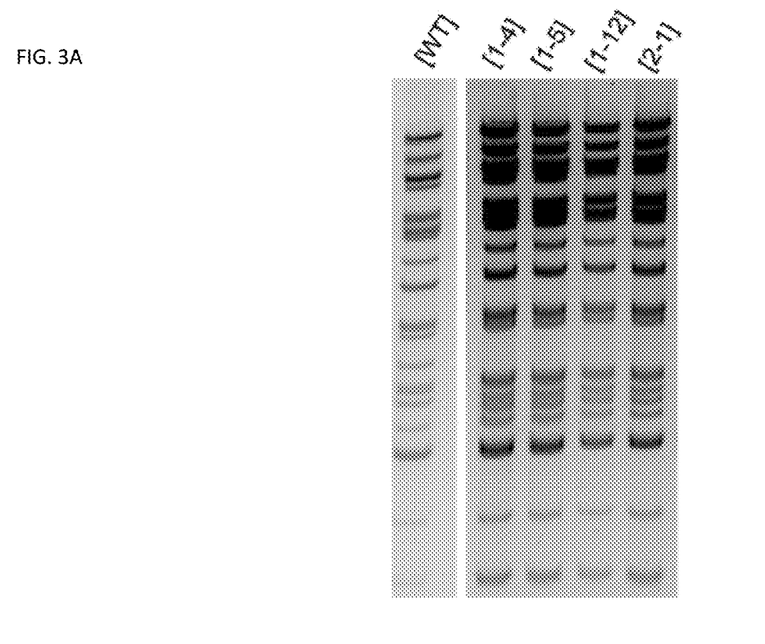
FIG. 3: Results of the embodiment of the method shown in FIG. 2. A) Genomic characterization of multiple EcoRI digested RhCMV EBOV (pRh25) BAC clones by DNA gel electrophoresis confirmed the absence of any gross genetic rearrangements. B) BAC DNA was then electroporated into RhCMV-permissive rhesus fibroblasts to reconstitute the RhCMV EBOV vaccine as a replicating virus. Virus was purified and expression of the EBOV GP target antigen was confirmed by western analysis of infected cell lysates.

FIG. 3A) Genomic characterization of multiple EcoRI digested RhCMV EBOV (pRh25) BAC clones by DNA gel electrophoresis confirmed the absence of any gross genetic rearrangements.

Figure 3B:
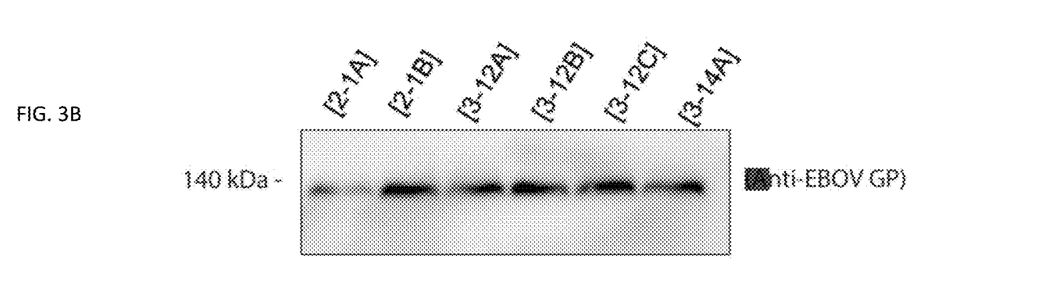

FIG. 3B) BAC DNA was then electroporated into RhCMV-permissive rhesus fibroblasts to reconstitute the RhCMV EBOV vaccine as a replicating virus. Virus was purified and expression of the EBOV GP target antigen was confirmed by western analysis of infected cell lysates.

Figure 4:
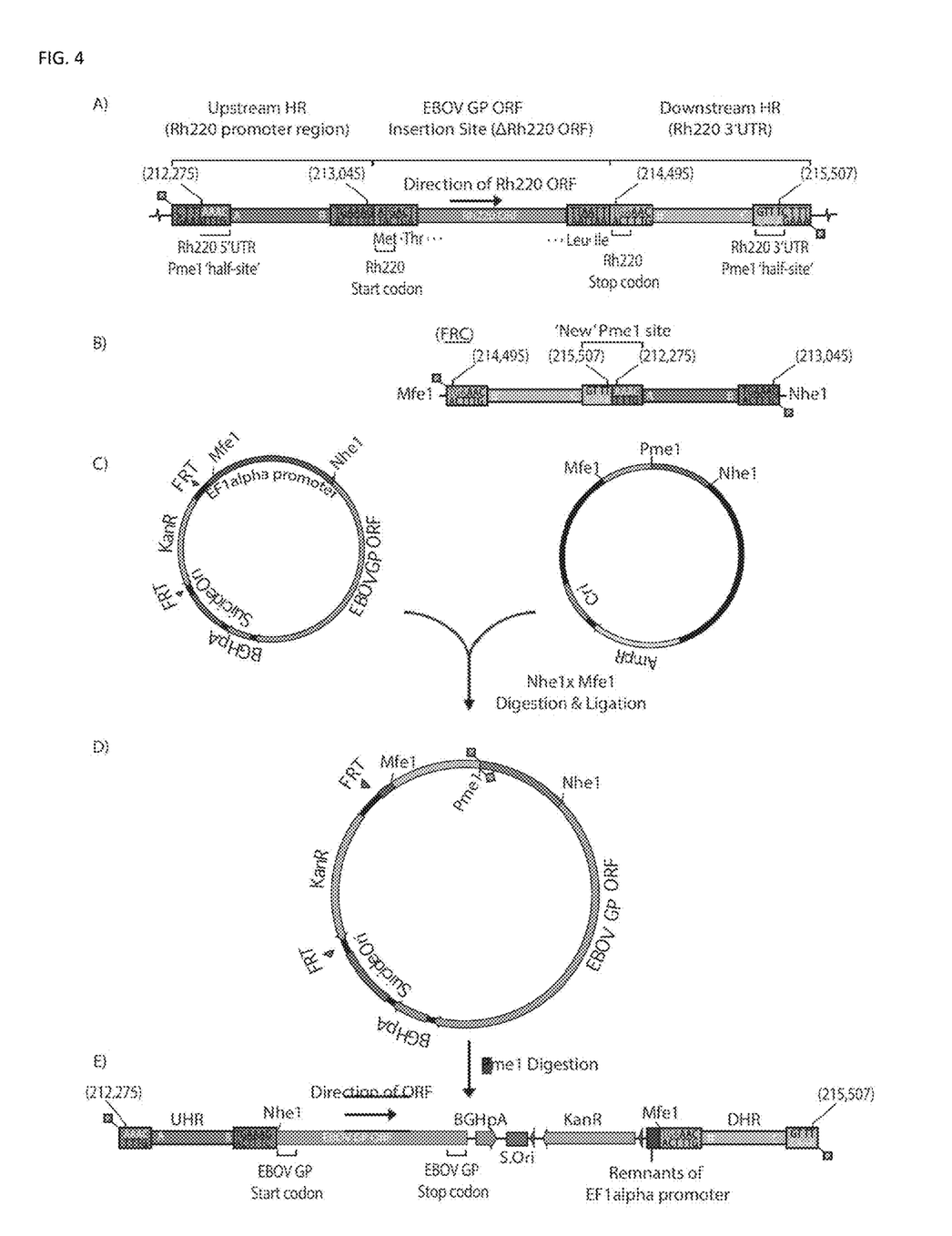

FIGS. 4 and 5—Reduction to Practice, Example 2. Using the Invention to Clone GP of EBOV Under Control of the Endogenous RhCMV Rh220 Promoter, Thereby Producing a Recombinant RhCMV Expressing EBOV GP Under the RhCMV Rh220 Promoter.

Cloning of GP EBOV Under Control of Rh220 Endogenous Promoter.

FIG. 4A) Schematic for insertion of EBOV GP within rhesus cytomegalovirus (RhCMV) genome to place under control of endogenous Rh220 (U528.5) (E) promoter. 'A' (5'-AAAC-3') and 'C' (5'-AAAC-3' on reverse strand) represent endogenous 'half sites' of PmeI (GTTTAAAC) in flanking homology region (HR) upstream and downstream of target site for insertion. PmeI was selected based on i) its absence from flanking regions, and ii) absence from within the suicide-based vectors containing the EBOV GP for insertion.

FIG. 4B) FRC with the 'new' single PmeI site and necessary restriction sites (Nhe 1 and MfeI) for insertion into the pminiOri (suicide-based vector) was synthesized (using an AmpR carrier vector from GeneArt from Invitrogen).

FIG. 4C) The FRC was cloned into the pminiOri (suicide-based vector) containing the EBOV GP for insertion into the RhCMV genome.

FIG. 4D) Schematic of resulting plasmid.

FIG. 4E) PmeI digestion was used to linearize the recombination fragment, which contains the necessary flanking HR for E/T or CrispR-based recombination within the RhCMV genome. 5' Phosphate residues are shown for DNA strand orientation.

Figure 5A:
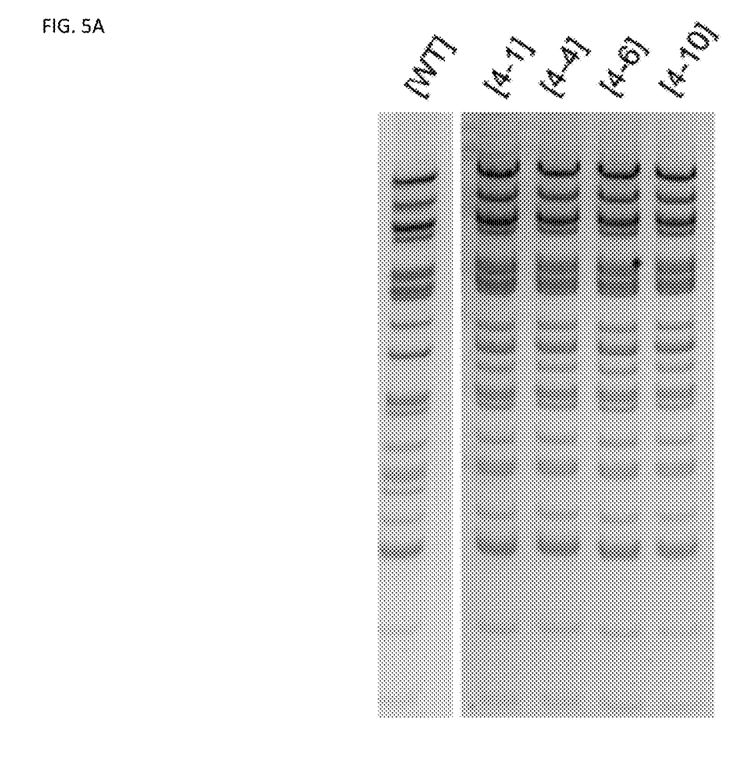
FIG. 5: Results of the method shown in FIG. 4. A) Genomic characterization of multiple EcoRI digested RhCMV EBOV (pRh220) BAC clones by DNA gel electrophoresis confirmed the absence of any gross genetic rearrangements. B) BAC DNA was then electroporated into RhCMV-permissive rhesus fibroblasts to reconstitute the RhCMV EBOV vaccine as a replicating virus. Virus was purified and expression of the EBOV GP target antigen was confirmed by western analysis of infected cell lysates.

FIG. 5A) Genomic characterization of multiple EcoRI digested RhCMV EBOV (pRh220) BAC clones by DNA gel electrophoresis confirmed the absence of any gross genetic rearrangements.

Figure 5B:
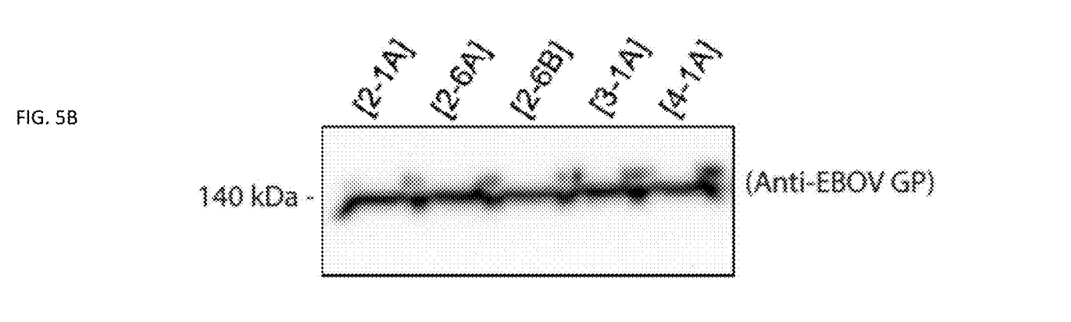

FIG. 5B) BAC DNA was then electroporated into RhCMV-permissive rhesus fibroblasts to reconstitute the RhCMV EBOV vaccine as a replicating virus. Virus was purified and expression of the EBOV GP target antigen was confirmed by western analysis of infected cell lysates.

Figure 6:
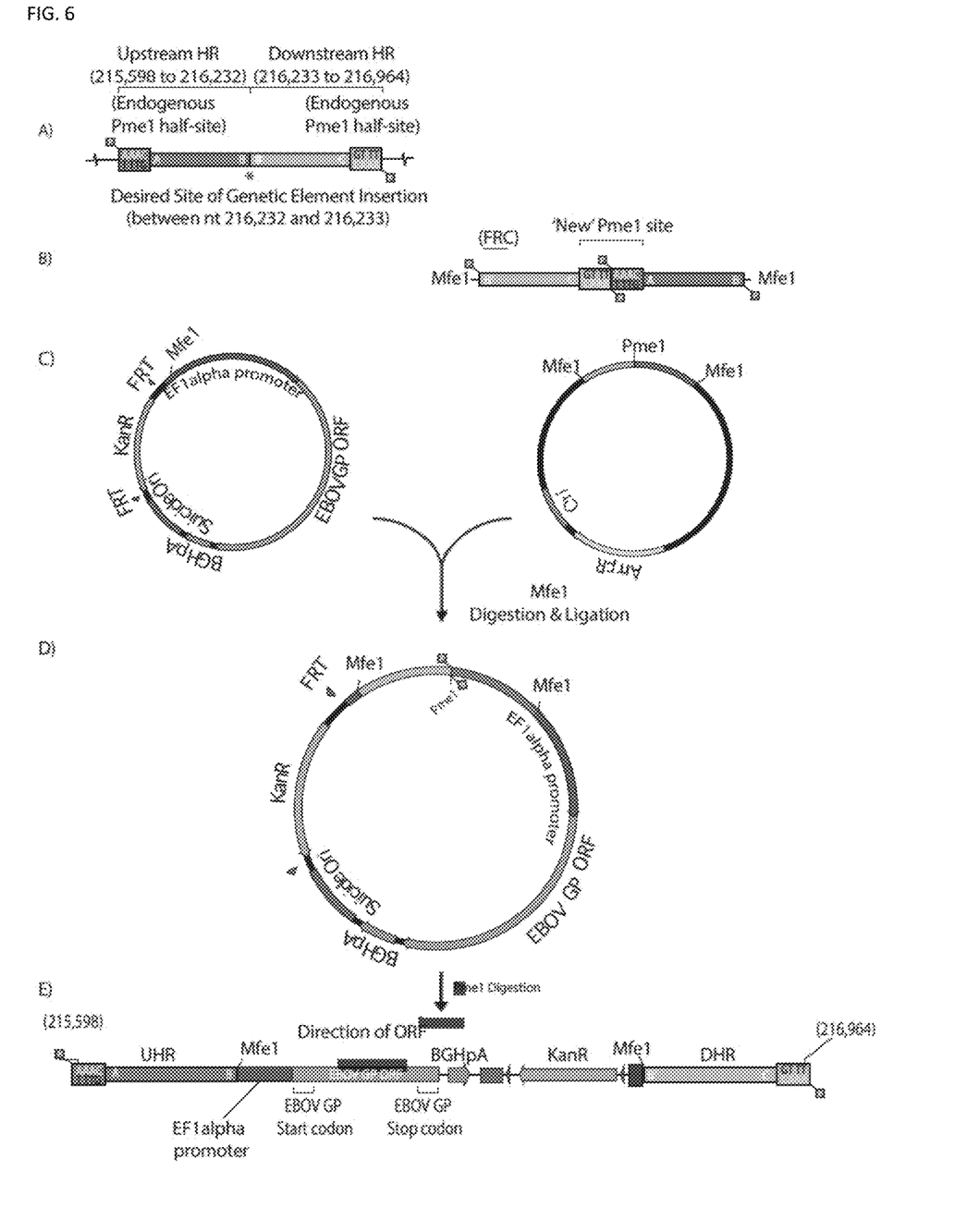
Figure 7:
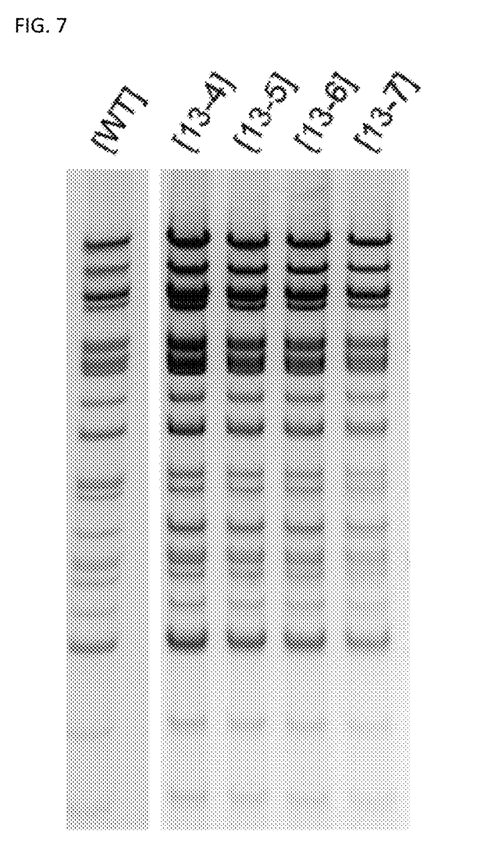
FIG. 7: Results of the method shown in FIG. 6. Genomic characterization of multiple EcoRI digested RhCMV EBOV (pEFIalpha) BAC clones by DNA gel electrophoresis confirmed the absence of any gross genetic rearrangements.

FIGS. 6 and 7—Reduction to Practice, Example 3. Using the Invention to Clone GP of EBOV Under Control of the Heterologous Human EFI Alpha Promoter, Thereby Producing a Recombinant RhCMV Expressing EBOV GP Under the Human EFI Alpha Promoter.

Reduction to Practice of EZ Recombination System II.

FIG. 6A) Schematic for insertion of EBOV GP within rhesus cytomegalovirus (RhCMV) genome to place under control of a heterologous promoter. 'A' (5'-AAAC-3') and 'C' (5'-AAAC-3' on reverse strand) represent endogenous 'half sites' of PmeI (GTTTAAAC) in flanking homology region (HR) upstream and downstream of target site for insertion. PmeI was selected based on i) its absence from flanking regions, and ii) absence from within the suicide-based vectors containing the EBOV GP for insertion.

FIG. 6B) FRC with the 'new' single PmeI site and necessary restriction site (Mfe 1) for insertion into the pminiOri (suicide-based vector) was synthesized (using an AmpR carrier vector from Gene-Art from Invitrogen).

FIG. 6C) The FRC was cloned into the pminiOri (suicide-based vector) containing the EBOV GP for insertion into the RhCMV genome.

FIG. 6D) Schematic of resulting plasmid.

FIG. 6E) PmeI digestion was used to linearize the recombination fragment, which contains the necessary flanking HR for E/T based recombination within the RhCMV genome. 5' Phosphate residues are shown for DNA strand orientation.

FIG. 7 Genomic characterization of multiple EcoRI digested RhCMV EBOV (pEFI alpha) BAC clones by DNA gel electrophoresis confirmed the absence of any gross genetic rearrangements.

Figure 8:
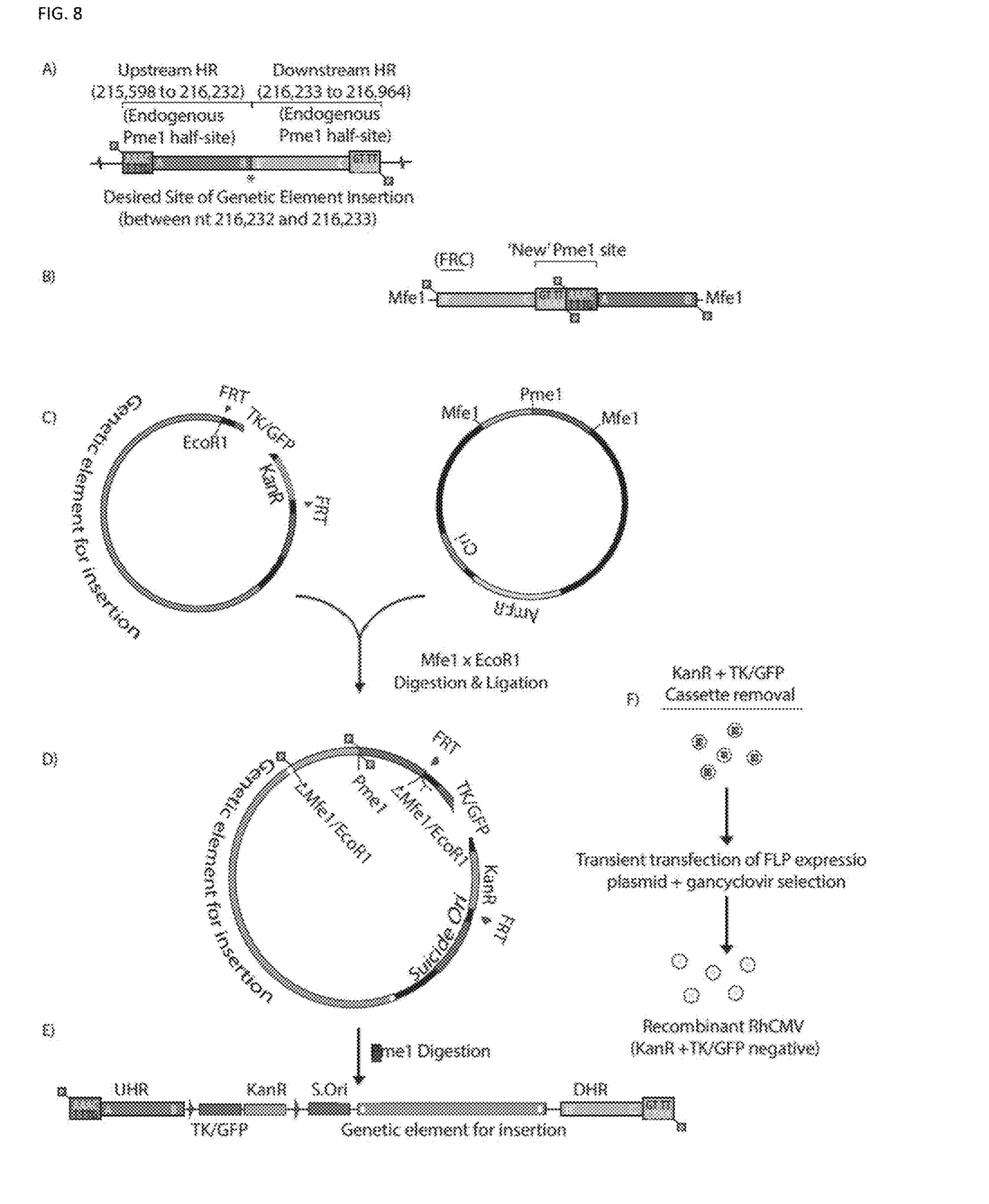

FIG. 8—Overview of EZ-Recombination System with Proposed Use of CrispR/Cas9 Technology Using Cloning of GP of EBOV Under Control of the Heterologous Human EFI Alpha Promoter as an Example.

Overview of EZ-Recombination System for Construction of Recombination Fragment to Insert EFI Alpha-GP into RhCMV (Between Rh213 and Rh214) Using CrispR/Cas9 Technology.

FIG. 8A) For CrispR/Cas9 recombination, HR regions of >500nt are required (Russell et al., 2015). Therefore, selected PmeI half sites located 634 bp upstream (nt 215, 598) and 731 bp (nt 216,964) downstream of desired site of insertion (*) (between 216,232 and 216,233).

FIG. 8B) FRC with the 'new' single PmeI site, as well as MfeI sites for insertion into EcoRI of pminiOri EFIalpha/EBOV GP (a suicide-based vector) will be synthesized (using an AmpR carrier vector—gene synthesis performed by GeneArt from Invitrogen).

FIG. 8C) The FRC will be cloned into the EFI alpha EBOV/GP miniOri for insertion into the RhCMV genome. Note: presence of endogenous EcoRI site within the 5'UTR HR necessitates use of MfeI for cloning into pminiOri EFIalpha/EBOV GP EcoRI site.

FIG. 8D) Schematic of resulting plasmid. Note: EFI alpha EBOVGP ORF runs in X to Y direction on 'Genetic Element for Insertion'.

FIG. 8E) PmeI digestion will be used to linearize the recombination fragment, which now contains the necessary anking homology regions (HR) for CrispR/Cas9-based recombination within the RhCMV genome.

FIG. 8F) The frt-flanked KanR+TK/GFP cassette is removed from recombinant RhCMV virus genome by co-expression of FLP recombinase (using a FLP expression plasmid) in the presence of negative selection for TK (gancyclovir). 5' Phosphate residues are shown for DNA strand orientation. (*) Site for genetic element insertion within RhCMV genome (numbering based on Malouli et al. 2012; Acc # JQ795930) within rh213 and Rh214 intergenic region. 'A' (5'-AAAC-3') and 'C' (5'-AAAC-3' on reverse strand) represent endogenous 'half sites' of PmeI: GTT-TAAAC (a rare 8nt cutter).

Although illustrative embodiments of the invention have been disclosed in detail herein, with reference to the accompanying drawings, it is understood that the invention is not limited to the precise embodiments shown and that various changes and modifications can be effected therein by one skilled in the art without departing from the scope of the invention.

REFERENCES

Jones, K. E., et al. Global trends in emerging infectious diseases. Nature 451, 990-993 (2008). Bi, Y., et al. High-efficiency targeted editing of large viral genomes by RNA-guided nucleases. PLoS Path 10, el004090 (2014).

Freuling, C. M., et al. The elimination of fox rabies from Europe: determinants of success and lessons for the future. Philos Trans R Soc Lond B Biol Sci 368, 20120142 (2013).

Mocarski, E. S. J., Shenk, T. & Pass, R. F. Cytomegalovirus. in Fields Virology, Vol. 2 (eds. Fields, B. N., Knipe, D. M. & Howley, P. M.) 2701-2772 (Lippincott-Raven Publishers, Philadelphia, 2007).

Boppana, S. B., Rivera, L. B., Fowler, K. B., Mach, M. & Britt, W. J. Intrauterine transmission of cytomegalovirus to infants of women with preconceptional immunity. N Engl J Med344, 1366-1371 (2001).

Adler, S. P. Molecular epidemiology of cytomegalovirus: evidence for viral transmission to parents from children infected at a day care center. Pediatr Infect Dis 5, 315-318. (1986).

Tsuda, Y., et al. Protective efficacy of a bivalent recombinant vesicular stomatitis virus vaccine in the Syrian hamster model of lethal Ebola virus infection. J Inf Dis 204 Suppl 3, S 1090-1097 (2011).

Tsuda, Y., et al. A cytomegalovirus-based vaccine provides long-lasting protection against lethal Ebola virus challenge after a single dose. Vaccine 33, 2261-2266 (2015).

Marsh, A. K., et al. Examining the species-specificity of rhesus macaque cytomegalovirus (RhCMV) in cynomolgus macaques. PLoS One 10, e0121339 (2015).

Murthy, S., et al. Absence of frequent herpesvirus transmission in a nonhuman primate predator-prey system in the wild. J Virol 87, 10651-10659 (2013).

Hansen, S. G., et al. Effector memory T cell responses are associated with protection of rhesus monkeys from mucosal simian immunodeficiency virus challenge. Nature Medicine 15, 293-299 (2009).

Hansen, S. G., et al. Profound early control of highly pathogenic SIV by an effector memory T-cell vaccine. Nature 473, 523-527 (2011).

Hansen, S. G., et al. Corrigendum: Immune clearance of highly pathogenic SIV infection. Nature 514, 654 (2014).

Hansen, S. G., et al. Immune clearance of highly pathogenic SIV infection. Nature 502, 100-104 (2013).

Safronetz, D., et al. A recombinant vesicular stomatitis virus-based Lassa fever vaccine protects guinea pigs and macaques against challenge with geographically and genetically distinct Lassa viruses. PLoS Negl Trop Dis 9, e0003736 (2015).

Geisbert, T. W., et al. Development of a new vaccine for the prevention of Lassa fever. PLoS Med 2, e183 (2005).

Safronetz, D., et al. Detection of Lassa virus, *Mali*. Emerg Infect Dis 16, 1123-1126 (2010).

Safronetz, D., et al. Geographic distribution and genetic characterization of Lassa virus in sub-Saharan Mali. PLoS Neg. Trop Dis 7, e2582 (2013).

Sogoba, N., Feldmann, H. & Safronetz, D. Lassa fever in West Africa: evidence for an expanded region of endemicity. Zoonoses and Public Health 59 Suppl 2, 43-47 (2012).

Ceballos G, Ehrlich P E, Barnosky A D et al. Accelerated modern human-induced species losses: Entering the sixth mass extinction. Sci Adv, 1(1), e1400253 (2015).

Morens D M, Folkers G K, Fauci A S. The challenge of emerging and re-emerging infectious diseases. Nature, 430(6996), 242-249 (2004).

Keesing F, Belden L K, Daszak P et al. Impacts of biodiversity on the emergence and transmission of infectious diseases. Nature, 468(7324), 647-652 (2010).

Jones K E, Patel N G, Levy M A et al. Global trends in emerging 5 infectious diseases. Nature, 451(7181), 990-993 (2008).

Jones B A, Grace D, Kock R et al. Zoonosis emergence linked to agricultural intensification and environmental change. PNAS USA, 110(21), 8399-8404 (2013).

Heesterbeek H, Anderson R M, Andreasen V et al. Modeling infectious disease dynamics in the complex landscape of global health. Science, 347(6227), aaa4339 (2015).

Mari Saez A, Weiss S, Nowak K et al. Investigating the zoonotic origin of the West African Ebola epidemic. EMBO Mol Med, 7(1), 17-23 (2015).

Cenciarelli O, Pietropaoli S, Malizia A et al. Ebola virus disease 2013-2014 outbreak in west Africa: an analysis of the epidemic spread and response. Int J Microbiol, [Epub ahead of print] (2015).

Gostin L O, Friedman E A. A retrospective and prospective analysis of the west African Ebola virus disease epidemic: robust national health systems at the foundation and an empowered WHO at the apex. Lancet, 385(9980), 1902-1909 (2015).

Committee on Alternative Models for the Federal Funding of Science. Advancing Research in Science and Engineering: Investing in Early-Career Scientists and High-Risk, High-Reward Research. Sciences, American Academy of Arts and Sciences (Eds) (Cambridge, Mass.) (2008).

Liu W, Li Y, Learn G H et al. Origin of the human malaria parasite *Plasmodium falciparum* in gorillas. Nature, 467 (7314), 420-425 (2010).

Diamond J. Evolution, consequences and future of plant and animal domestication. Nature, 418(6898), 700-707 (2002).

Field H E. Bats and emerging zoonoses: henipaviruses and SARS. Zoonoses and public health, 56(6-7), 278-284 (2009).

Swayne D E. Impact of vaccines and vaccination on global control of avian influenza. Avian Dis, 56(4 Suppl), 818-828 (2013).

Freuling C M, Hampson K, Selhorst T et al. The elimination of fox rabies from Europe: determinants of success and lessons for the future. Philos Trans R Soc Lond B Biol Sci, 368(1623), 20120142 (2013).

Bielby J, Donnelly C A, Pope L C et al. Badger responses to small-scale culling may compromise targeted control of bovine tuberculosis. PNAS USA, 111(25), 9193-9198 (2014).

Indran S V, Ikegami T. Novel approaches to develop Rift Valley fever vaccines. Front Cell Infect Microbiol, 2, 131 (2012).

Whitehouse C A. Crimean-Congo hemorrhagic fever. Antiviral Res, 64(3), 145-160 (2004).

Mahl P, Cliquet F, Guiot A L et al. Twenty year experience of the oral rabies vaccine SAG2 in wildlife: a global review. Vet Res, 45(1), 77 (2014).

20 Barcena J, Morales M, Vazquez B et al. Horizontal transmissible protection against myxomatosis and rabbit hemorrhagic disease by using a recombinant myxoma virus. J Virol, 74(3), 1114-1123 (2000).

Barcena J, Pages-Mante A, March R et al. Isolation of an attenuated myxoma virus field strain that can confer protection against myxomatosis on contacts of vaccinates. Arch Virol, 145(4), 759-771 (2000).

Spiesschaert B, McFadden G, Hermans K et al. The current status and future directions of myxoma virus, a master in immune evasion. Vet Res, 42, 76 (2011).

Torres J M, Sanchez C, Ramirez M A et al. First field trial of a transmissible recombinant vaccine against myxomatosis and rabbit hemorrhagic disease. Vaccine, 19(31), 4536-4543 (2001).

Mocarski E S J, Shenk T, Pass R F. Cytomegalovirus. In: Fields Virology. Fields, B N, Knipe, D M, Howley, P M (Eds.) (Lippincott-Raven Publishers, Philadelphia) 2701-2772 (2007).

Boppana S B, Rivera L B, Fowler K B et al. Intrauterine transmission of cytomegalovirus to infants of women with preconceptional immunity. N Engl J Med, 344(18), 1366-1371 (2001).

Adler S P. Molecular epidemiology of cytomegalovirus: evidence for viral transmission to parents from children infected at a day care center. Pediatr Infect Dis, 5(3), 315 318. (1986).

Marsh A K, Ambagala A P, Perciani C T et al. Examining the species-specificity of rhesus macaque cytomegalovirus (RhCMV) in cynomolgus macaques. PLoS One, 10(3), e0121339 (2015).

Murthy S, Couacy-Hymann E, Metzger S et al. Absence of frequent herpesvirus transmission in a nonhuman primate predator-prey system in the wild. J Virol, 87(19), 10651-10659 (2013).

Lloyd M L, Shellam G R, Papadimitriou J M et al. Immunocontraception is induced in BALB/c mice inoculated with murine cytomegalovirus expressing mouse zona pellucida 3. Biol Reprod, 68(6), 2024-2032 (2003). Lloyd M L, Papadimitriou J M, O'Leary S et al. Immunoglobulin to zona pellucida 3 mediates ovarian damage and infertility after contraceptive vaccination in mice. J Autoimmun, 35(1), 77-85 (2010).

Redwood A J, Smith L M, Llyod M L et al. Prospects for virally vectored immunocontraception in the control of wild house mice (Mus domesticus). Wildlife Research, 34, 530-539 (2007).

Rizvanov A A, van Geelen A G, Morzunov S et al. Generation of a recombinant cytomegalovirus for expression of a hantavirus glycoprotein. J Virol, 77(22), 12203-12210 (2003).

Rizvanov A A, Khaiboullina S F, van Geelen A G et al. Replication and immunoactivity of the recombinant *Peromyscus maniculatus* cytomegalovirus expressing hantavirus GI glycoprotein in vivo and in vitro. Vaccine, 24(3), 327-334 (2006).

Deere J D, Barry P A. Using the nonhuman primate model of HCMV to guide vaccine development. Viruses, 6(4), 1483-1501 (2014).

Tsuda Y, Parkins C J, Caposio P et al. A cytomegalovirus-based vaccine provides long-lasting protection against lethal Ebola virus challenge after a single dose. Vaccine, 33(19), 2261-2266 (2015).

Tsuda Y, Safronetz D, Brown K et al. Protective efficacy of a bivalent recombinant vesicular stomatitis virus vaccine in the Syrian hamster model of lethal Ebola virus infection. J Inf. Dis, 204 Suppl 3, SI090-1097 (2011).

Groseth A, Hoenen T, Alimonti J B et al. In vitro evaluation of antisense RNA efficacy against Filovirus infection, by use of reverse genetics. J Inf Dis, 196 Suppl 2, 5382-389 (2007).

Ghai R. Ebola: outbreaks cause crisis for great apes and humans. The Jane Goodall Institute of Canada, (Eds) (2014)

Keele B F, Jones J H, Terio K A et al. Increased mortality and AIDS-like immunopathology in wild chimpanzees infected with SIVcpz. Nature, 460(7254), 515-519 (2009).

USAID. USAID launches Emerging Pandemic Disease Threats Program. (2009). Bi Y, Sun L, Cao D et al. High-efficiency targeted editing of large viral genomes by RNA-guided nucleases. PLoS pathogens, 10(5), e1004090 (2014).

WHO. Influenza. (Eds) http://www.who.int/mediacetre/factsheets/2003/fs211/enl (2015). [Accessed 7 July 15]

Knobel D L, Cleaveland S, Coleman P G et al. Re-evaluating the burden of rabies in Africa and Asia. Bull World Health Organ, 83(5), 360-368 (2005).

Budke C M, Deplazes P, Torgerson P R. Global socioeconomic impact of cystic echinococcosis. Emerg Infect Dis, 12(2), 296-303 (2006).

Torgerson P R, Torgerson D J. Public health and bovine tuberculosis: what's all the fuss about? Trends Microbiol, 18(2), 67-72 (2010).

Mafojane N A, Appleton C C, Krecek R C et al. The current status of neurocysticercosis in Eastern and Southern Africa. Acta Trop, 87(1), 25-33 (2003). Salgado P, Rojas R, Sotelo J. Cysticercosis. Clinical classification based on imaging studies. Arch Intern Med, 157(17), 1991-1997 (1997).

Moncayo A, Ortiz Yanine M I. An update on Chagas disease (human American trypanosomiasis). Ann Trop Med Parasitol, 100(8), 663-677 (2006). Van den Bossche P, de La Rocque S, Hendrickx G et al. A changing environment and the epidemiology of tsetse-transmitted livestock trypanosomiasis. Trends Parasitol, 26(5), 236-243 (2010).

Lecompte E, Fichet-Calvet E, Daffis S et al. Mastomys natalensis and Lassa fever, West Africa. Emerg Infect Dis, 12(12), 1971-1974 (2006).

Falzarano D, Feldmann H. Vaccines for viral hemorrhagic fevers—progress and shortcomings. Curr Opin Virol, 3(3), 343-351 (2013), Evangelista K V, Coburn J. Leptospira as an emerging pathogen: a review of its biology, pathogenesis and host immune responses. Future Microbiol, 5(9), 1413-1425 (2010), Volz A, Kupke A, Song F et al. Protective efficacy of recombinant Modified Vaccinia virus Ankara (MVA) delivering Middle East Respiratory Syndrome coronavirus spike glycoprotein. J Virol, [Epub ahead of print] (2015).

A Programmable Dual-RNA-Guided DNA Endonuclease in Adaptive Bacterial Immunity Martin Jinek et al 17 Aug. 2012, 337 (6096): 816-821.

What is claimed:

1. A method to construct a herpesvirus genome for use in making a herpesvirus-based vaccine, said method comprising:
   a. identifying a desired site of insertion for a genetic element in a target herpesvirus genome;
   b. locating an endogenous, native, half-site of a selected restriction endonuclease present upstream of the site within the herpesvirus genome to be targeted for genetic manipulation and thereby defining the 5' extent of an upstream homology region, in which said selected restriction endonuclease is an at least eight nucleotide cutter and results in a cut in a complete restriction site that includes the restriction half-site;
   c. locating an endogenous, native, half-site of the same selected at least eight nucleotide cutter restriction endonuclease present downstream of the site within the herpesvirus genome to be targeted for genetic manipulation and thereby defining the 3' extent of a downstream homology region;
   d. synthesizing a flanking region cassette (FRC) comprising the upstream and downstream endogenous half-sites and forming the complete restriction site for the selected restriction endonuclease flanked by said upstream and downstream homology regions;
   e. inserting the FRC into a plasmid vector which includes the genetic element to be used to manipulate the target herpes virus genome, conferring upon the genetic element the upstream and downstream homology regions necessary for recombination within said target herpesvirus genome at the desired site of insertion;
   f. linearizing the plasmid vector using the selected restriction endonuclease to cut within the FRC to form the genetic element with the upstream and downstream homology regions; and
   g. recombining the linearized plasmid vector into the target herpesvirus viral genome.

2. The method of claim 1, in which the restriction endonuclease site is not present within either the flanking homology region or genetic element.

3. The method of claim 1, in which the upstream and downstream homology regions are at least 50 nucleotides in length.

4. The method of claim 1, in which the upstream and downstream homology regions are at least 500 nucleotides in length.

5. The method of claim 1, in which said selected restriction endonuclease is a blunt ended cutter.

6. The method of claim 1, in which the plasmid vector is recombined within the target viral genome DNA using E/T-based or CrispR/Cas9-based technology.

7. A method as claimed in claim 1, in which the target herpesvirus genome is CMV-based.

8. A method as claimed in claim 1, in which the target herpesvirus genome is selected from Human CMV (HCMV), Simian CMV (SCCMV), Rhesus CMV (RhCMV), Chimpanzee CMV (CCMV), Murine CMV (MCMV), and Gorilla CMV (GCMV).

9. A method to construct a plasmid vector for use in making a herpesvirus-based vaccine, the method comprising:
   a. identifying a desired site of insertion for a genetic element in a target herpesvirus genome;
   b. locating an endogenous, native, half-site of a selected restriction endonuclease present upstream of the site within the herpesvirus genome to be targeted for genetic manipulation and thereby defining the 5' extent of an upstream homology region in which said selected restriction endonuclease is an at least eight nucleotide cutter and in which said restriction endonuclease results in a cut in a complete restriction site that includes the restriction half-site;
   c. locating an endogenous, native, half-site of the same selected at least eight nucleotide cutter restriction endonuclease present downstream of the site within the herpesvirus genome DNA to be targeted for genetic manipulation and thereby defining the 3' extent of a downstream homology region;
   d. synthesizing a flanking region cassette (FRC) comprising the upstream and downstream endogenous half-sites forming the complete restriction site for the selected restriction endonuclease flanked by said upstream and downstream homology regions; and
   e. inserting the FRC into a plasmid vector which includes the genetic element to be used to manipulate the target herpesvirus genome, conferring upon the genetic element the necessary flanking homology regions for subsequent recombination within the target viral genome DNA at the desired site of insertion.

10. The method of claim 9, in which said selected restriction endonuclease is a blunt ended cutter.

11. The method of claim 9, in which the plasmid vector is recombined within the target viral genome DNA using E/T-based or CrispR/Cas9-based technology.

12. A method to construct a herpesvirus genome useful in making a herpesvirus-based vaccine against an emerging infectious disease pathogen, said method comprising the steps of:

A) identifying a desired site of insertion for a genetic element in a target herpesvirus genome DNA;

B) locating an endogenous half-site of a selected restriction endonuclease present upstream of the site within the target herpesvirus genome DNA to be targeted for genetic manipulation and thereby defining the 5' extent of an upstream homology region, in which said selected restriction endonuclease is a rare cutter;

C) locating an endogenous half-site of the same selected rare cutter restriction endonuclease present downstream of the site within the herpesvirus genome DNA to be targeted for genetic manipulation and thereby defining the 3' extent of a downstream homology region;

D) synthesising a flanking region cassette (FRC) including said upstream and downstream homology regions, said upstream and downstream homology regions appearing in FRC in the opposite order to that which they are found in the herpesvirus genome DNA, resulting in juxtapositioning of said upstream and downstream flanking homology regions and causing formation of a complete restriction site for the selected restriction endonuclease flanked by the homology regions; and E) inserting the FRC into a plasmid vector which includes the genetic element to be used to manipulate the target viral genome DNA and linearizing said plasmid vector using the selected rare cutter restriction endonuclease to cut within the FRC, conferring upon the genetic element the necessary flanking homology regions for recombination within said target herpesvirus genome DNA at the desired site of insertion; and F) recombining the linearized plasmid vector into a herpesvirus genome at the desired site of insertion.

* * * * *